United States Patent [19]

Beestman et al.

[11] 4,280,833

[45] Jul. 28, 1981

[54] ENCAPSULATION BY INTERFACIAL POLYCONDENSATION, AND AQUEOUS HERBICIDAL COMPOSITION CONTAINING MICROCAPSULES PRODUCED THEREBY

[75] Inventors: George B. Beestman, Creve Coeur; John M. Deming, Hazelwood, both of Mo.

[73] Assignee: Monsanto Company, St. Louis, Mo.

[21] Appl. No.: 23,566

[22] Filed: Mar. 26, 1979

[51] Int. Cl.³ .................... A01N 37/18; A01N 37/22; B01J 13/02

[52] U.S. Cl. .......................................... 71/100; 71/3; 71/64 F; 71/93; 71/118; 71/120; 71/121; 71/DIG. 1; 252/316; 424/19; 424/32

[58] Field of Search ................ 252/316; 71/64 F, 118, 71/100

[56] References Cited

U.S. PATENT DOCUMENTS

| | | | |
|---|---|---|---|
| 3,429,827 | 2/1969 | Ruus | 252/316 |
| 3,464,926 | 9/1969 | Vandegaer et al. | 252/316 |
| 3,494,872 | 2/1970 | Maierson et al. | 252/316 |
| 3,551,132 | 12/1970 | Husted | 71/118 X |
| 3,576,760 | 4/1971 | Gould et al. | 424/32 X |
| 3,577,515 | 5/1971 | Vandegaer | 252/316 X |
| 3,663,200 | 5/1972 | Olin | 71/118 |
| 3,796,669 | 3/1974 | Kiritani et al. | 252/316 |
| 3,929,453 | 12/1975 | Dimitri et al. | 71/118 X |
| 3,959,464 | 5/1976 | DeSavigay | 424/32 X |
| 4,046,741 | 9/1977 | Scher | 252/316 X |

FOREIGN PATENT DOCUMENTS

| | | | |
|---|---|---|---|
| 1371179 | 10/1974 | United Kingdom | 424/32 |
| 1462542 | 1/1977 | United Kingdom | 424/32 |
| 1513614 | 6/1978 | United Kingdom | 424/32 |

*Primary Examiner*—Richard D. Lovering
*Attorney, Agent, or Firm*—Patricia A. Coburn; Donald W. Peterson

[57] ABSTRACT

This invention relates to a process for encapsulation, and particularly to the production of small or minute capsules constituted by a skin or thin wall of polyurea, which involves bringing together an aqueous phase containing a lignin sulfonate emulsifier and a water-immiscible phase containing a water-immiscible material, the material to be encapsulated, plus polymethylene polyphenylisocyanate, dispersing the water-immiscible phase in the aqueous phase followed by addition of a polyfunctional amine. Polymethylene polyphenylisocyanate reacts with the amine to form a solid polyurea shell wall about the encapsulated material. The capsules formed may be directly used as aqueous suspensions.

29 Claims, No Drawings

ENCAPSULATION BY INTERFACIAL POLYCONDENSATION, AND AQUEOUS HERBICIDAL COMPOSITION CONTAINING MICROCAPSULES PRODUCED THEREBY

BACKGROUND OF THE INVENTION

This invention relates to a process for producing small or minute capsules containing a water-immiscible material which comprises dissolving polymethylene polyphenylisocyanate in said water-immiscible material, the material to be encapsulated, dispersing the resulting mixture in an aqueous phase containing an emulsifier selected from the group consisting of the salts of lignin sulfonate and thereafter adding a polyfunctional amine, whereby the amine reacts with polymethylene polyphenylisocyanate to form oil-insoluble polyurea microcapsule walls about the water-immiscible material at the oil/water interface. The capsules may be produced to any desired size, for example, of the order of 1 micron up to 100 microns or larger, preferably the size of the microcapsules will range from about 1 to about 50 microns in diameter.

Capsules of this character have a variety of uses, as for containing dyes, inks, chemical reagents, pharmaceuticals, flavoring materials, pesticides, herbicides and the like. Any liquid, oil, meltable solid or solvent soluble material into which polymethylene polyphenylisocyanate can be dissolved and which is non-reactive with said isocyanate, may be encapsulated with this process. Once encapsulated, the liquid or other form is preserved until it is released by some means or instrumentality that breaks, crushes, melts, dissolves, or otherwise removes the capsule skin or until release by diffusion is effected under suitable conditions. The process of the invention is particularly suitable for the production of herbicide containing microcapsules of very small particle size, suspended in an aqueous solution.

Aqueous dispersions of pesticide and herbicide microcapsules are particularly useful in controlled release pesticide and herbicidal formulations because they can be diluted with water or liquid fertilizer and sprayed using conventional equipment, thereby producing uniform field coverage of the pesticide or herbicide. Additives such as film forming agents can be added directly to the finished formulation to improve the adhesion of microcapsules to foliage. In some cases, reduced toxicity and extended activity of encapsulated herbicides and pesticides have been noted.

A variety of techniques have heretofore been used or proposed for encapsulation purposes. In one such process, known as "simple coacervation", a polymer separates from a solvent solution of the polymer by the action of a precipitating agent that reduces the solubility of the polymer in the solvent (e.g., a salt or a non-solvent for the polymer). Patents describing such processes and their shell wall material include U.S. Pat. Nos. 2,800,458 (hydrophilic colloids); 3,069,370 and 3,116,216 (polymeric zein); 3,137,631 (denatured proteins); 3,418,250 (hydrophobic thermoplastic resins); and others.

Another method involves microencapsulation based on in situ interfacial condensation polymerization. British Pat. No. 1,371,179 discloses a process which consists of dispersing an organic pesticide phase containing a polymethylene polyphenylisocyanate or toluene diisocyanate monomer into an aqueous phase. The wall forming reaction is initiated by heating the batch to an elevated temperature at which point the isocyanate monomers are hydrolyzed at the interface to form amines, which in turn react with unhydrolyzed isocyanate monomers to form the polyurea microcapsule wall. One difficulty with this method is the possiblity of continued reaction of monomer after packaging. Unless all monomer is reacted during the preparation, there will be continued hydrolysis of the isocyanate monomer with evolution of $CO_2$, resulting in the development of pressure when the formulation is packaged.

Various methods of encapsulation by interfacial condensation between direct-acting, complimentary reactions are known. Within these methods are reactions for producing various types of polymers as the capsule walls. Many of such reactions to produce the coating substance occur between an amine, which must be of at least difunctional character and a second reactant intermediate, which for producing a polyurea is a difunctional or polyfunctional isocyanate. The amines chiefly used or proposed in these methods are typified by ethylene diamine, having at least 2 primary amino groups. U.S. Pat. No. 3,577,515 is illustrative of encapsulation by interfacial condensation.

U.S. Pat. No. 3,577,515 describes a continuous or batch method which requires a first reactant and a second reactant complimentary to the first reactant, with each reactant in separate phases, such that the first and second reactants react at the interface between the droplets to form encapsulated droplets. The process is applicable to a large variety of polycondensation reactions, i.e., to many different pairs of reactants capable of interfacial condensation from respective carrier liquids to yield solid film at the liquid interface. The resulting capsule skin may be produced as a polyamide, polysulfonamide, polyester, polycarbonate, polyurethane, polyurea or mixtures of reactants in one or both phases so as to yield corresponding condensation copolymers. The reference describes the formation of a polyurea skin when diamines or polyamines (e.g., ethylene diamine, phenylene diamine, toluene diamine, hexamethylene diamine and the like) are present in the water phase and diisocyanates or polyisocyanates (e.g., toluene diisocyanate, hexamethylene diisocyanate and polymethylene polyphenylisocyanate) are present in the organic/oil phase. In the practice of U.S. Pat. No. 3,577,515, the liquid which preponderates becomes the continuous phase liquid. That is, in forming oil containing microcapsules, the aqueous liquid would preponderate; when water encapsulated microcapsules are formed, the oil phase would preponderate.

Although a number of methods are available in the art for producing microencapsulated pesticide and herbicide formulations there are various disadvantages associated with the prior art methods. The encapsulated materials formed by the in situ interfacial polymerization process of British Pat. No. 1,371,179, require post-treatment to prevent continued carbon dioxide evolution and excessive caking, thereby increasing the costs of the finished product. For many processes of encapsulation, it is oftentimes necessary to separate the encapsulated material from the forming media. During the separation process, the capsule wall is subjected to great stresses and strains which can result in premature rupture of the capsules with concomitant loss of encapsulated material. These efforts also fall short of practical value in various other respects. Various experiments have indicated the difficulty in establishing the desired capsules in discreet form and avoiding coalescence of the partially formed capsules into a heterogenous mass of materials lacking distinct capsule formation. Control of capsule uniformity is troublesome in the prior art method. Very low concentrations of intended product relative to the total mixture are often obtained.

The present invention provides a new and improved encapsulation process which is rapid and effective and which avoids the necessity of separation of the encapsulated material from the continuous phase material. The present invention also eliminates the need for using a strong solvent in the organic phase resulting in a savings of energy, and packaging and equipment ware. In addition, direct combination of water-based herbicide and pesticide formulations are possible with other water-based pesticides.

The critical feature of the present invention resides in the use of lignin sulfonate emulsifiers, in particular, the salts of lignin sulfonate, as for example, the sodium, potassium, magnesium, calcium or ammonium salts, to achieve emulsions wherein a concentrated amount of water-immiscible material is present in the water-immiscible phase. Generally there will be greater than 480 grams per liter of water-immiscible material present. By use of the particular emulsifiers described herein, it is possible to retain the finished microcapsules in the original aqueous solution, thus avoiding the additional step of separation of the microcapsules from the original aqueous environment. Further, the finished microcapsules do not agglomerate nor does the aqueous capsule mass solidify when stored for extended periods of time or when exposed for short-terms to elevated temperatures.

The present invention is particularly advantageous when employed to encapsulate herbicides, especially the acetanilide and thiocarbamate herbicides like alachlor, butachlor, propachlor, triallate, diallate and the like. Experiments indicate that conventional oil/water herbicide emulsifiers fail to produce sufficiently stable emulsions to attain microencapsulation of concentrated amounts of herbicide materials and avoiding solidification of the oil/water mass when amine is added. Additionally, attempts to encapsulate concentrated amounts of acetanilide and thiocarbamate herbicides (four to five pounds per gallon) using traditional interfacial polymerization techniques, as for example that disclosed in U.S. Pat. No. 3,577,515, have resulted in unsatisfactory formulations because of the problem of herbicide crystal growth, as well as agglomeration or solidification of the finished suspensions. It is thought that herbicide crystal growth results from either incomplete encapsulation of the herbicidal material or from the passage of small amounts of herbicide through the polymeric shell wall. The problem is particularly acute with the acetanilide herbicides.

Crystal growth is very undesirable because once it occurs, the final formulations cannot be used directly; rather the microcapsules must be separated from the aqueous solution and resuspended in water before they can be sprayed in conventional agricultural herbicide and fertilizer spraying apparatus.

It is accordingly a particular object of this invention to provide a process whereby greater than 480 grams of acetanilide herbicides, e.g., alachlor, propachlor, butachlor and the like and thiocarbamate herbicides, e.g., triallate, diallate and the like, per liter of aqueous material, is encapsulated in a polyurea shell wall with the finished microcapsules being suspended in the original aqueous solution. The suspended microcapsules may be stored for extended periods of time and may be exposed for short-terms to elevated temperatures without the occurrence of agglomeration or solidification of the aqueous, capsule mass or herbicide crystal formation.

DETAILED DESCRIPTION OF THE INVENTION

The invention relates to a process of encapsulating a water-immiscible material within a shell wall of polyurea. The procedure of the invention involves first providing an aqueous solution containing an emulsifier selected from the group consisting of the salts of lignin sulfonate, for example, the sodium, potassium, magnesium, calcium or ammonium salts. Particularly effective for use herein, is the sodium salt of lignin sulfonate. A water-immiscible (organic) phase, which consists of a water-immiscible material (the material to be encapsulated) and polymethylene polyphenylisocyanate, is added to the aqueous phase, with agitation, to form a dispersion of small droplets of water-immiscible phase within the aqueous phase. Thereafter, a polyfunctional amine, preferably, 1,6-hexamethylene diamine, is added, with continued agitation, to the organic/aqueous dispersion. The polyfunctional amine reacts with polymethylene polyphenylisocyanate to form a capsular polyurea shell about the water-immiscible material.

The water-immiscible material referred to herein, is the material to be encapsulated and is suitably, any liquid, oil, meltable solid or solvent soluble material, into which polymethylene polyphenylisocyanate can be dissolved and is non-reactive thereto. Such water-immiscible materials as herbicides, e.g., $\alpha$-chloro-2',6'-diethyl-N-methoxymethyl acetanilide (commonly known as alachlor), N-butoxymethyl-$\alpha$-chloro-2',6'-diethylacetanilide (commonly known as butachlor), $\alpha$-chloro-N-isopropyl acetanilide (commonly known as propachlor), 2'-methyl-6'-ethyl-N-(1-methoxyprop-2-yl)-2-chloroacetanilide (commonly known as metolachlor), S-2,3,3-trichloroallyl-diisopropyl thiocarbamate (commonly known as triallate), S-2,3-dichloroallyl-diisopropylthiocarbamate (commonly known as diallate), $\alpha,\alpha,\alpha$-trifluoro-2,6-dinitro-N,N-dipropyl-p-toluidine (commonly known as trifluralin), 2-chloro-4-ethylamino-6-isopropylamino-1,3,5-triazine (commonly known as atrazine), 2-chloro-4,6-bis(ethylamino)-s-triazine (commonly known as simazine), 4-amino-6-(1,1-dimethylethyl)-3-(methylthio)-1,2-4-triazin-5(4H)one (commonly known as metribuzin), N-(-3,4-dichlorophenyl)-N'-methoxy-N'-methylurea (commonly known as linuron); insecticides, e.g., methyl and ethyl parathion, pyrethrin and pyrethroids (e.g., permethrin and fenvalerate); and organic solvents, e.g., xylene and monochlorobenzene are specifically contemplated herein.

In the practice of the preferred embodiment of the present invention, the material to be encapsulated is a herbicide, particularly an acetanilide or thiocarbamate herbicide and more particularly alachlor, butachlor, propachlor, triallate and diallate herbicides.

The material to be encapsulated utilizing the process of the present invention need not consist of only one type, but may be a combination of two or more various types of water-immiscible materials. For example, employing an appropriate water-immiscible material, such a combination is an active herbicide with another active herbicide or an active herbicide and an active insecticide. Also contemplated is a water-immiscible material to be encapsulated which comprises an active ingredient, such as a herbicide, and an inactive ingredient, such as a solvent or adjuvant.

The water-immiscible material containing the dissolved polymethylene polyphenylisocyanate comprises the water-immiscible or organic phase. The water-immiscible material acts as the solvent for polymethylene polyphenylisocyanate thus avoiding the use of other water-immiscible organic solvents and allowing for a concentrated amount of water-immiscible material in the final encapuslated product. The water-immiscible material and polymethylene polyphenylisocyanate are added simultaneously to the aqueous phase in a pre-mixed state. That is, the water-immiscible material and polymethylene polyphenylisocyanate are pre-mixed to obtain a homogeneous water-immiscible phase before addition to and emulsification in the aqueous phase.

The concentration of water-immiscible material initially present in the water-immiscible phase should be sufficient to provide at least 480 grams of water-immiscible material per liter of aqueous solution. However, this is by no means limiting and a greater amount can be used. In practical operation, as will be recognized by those skilled in the art, the use of extremely high concentrations of water-immiscible material will result in very thick suspensions of microcapsules. In general, the concentration of water-immiscible material will range from about 480 grams to about 700 grams per liter of aqueous solution. The preferred range is from about 480 grams to about 600 grams per liter of aqueous solution.

The polyisocyanate useful in this process is polymethylene polyphenylisocyanate. Suitable for use herein are the following commercially available polymethylene polyphenylisocyanates: PAPI ® and PAPI-135 ® (registered trademarks of the Upjohn Co.) and Mondur-MR ® (registered trademark of the Mobay Chemical Company).

The polyfunctional amines suitable for use in the present invention are those amines which are capable of reacting with polymethylene polyphenylisocyanate to form a polyurea shell wall. The polyfunctional amines should be water-soluble per se or in water soluble salt form. The usable polyfunctional amines can be selected from a wide range of such materials. Suitable examples of polyfunctional amines which may be used in this invention include, but are by no means limited to the following: ethylenediamine, propylenediamine, isopropylenediamine, hexamethylenediamine, toluenediamine, ethenediamine, triethylenetetraamine, tetraethylenepentamine, pentaethylenehexamine, diethylenetriamine, bis-hexamethylenetriamine and the like. The amines may be used alone or in combination with each other, preferably in combination with 1,6-hexamethylenediamine (HMDA). 1,6-hexamethylenediamine is preferred for use in the process of the present invention.

Polymethylene polyphenylisocyanate and the polyfunctional amine form the shell wall which ultimately encapsulates the water-immiscible material. The shell wall content of the capsules formed by the present process may vary from about 5 percent to about 30 percent, preferably 8 to 20 percent and more particularly, 10 percent by weight, of the water-immiscible material.

The amount of polymethylene polyphenylisocyanate and polyfunctional amine used in the process is determined by the percent shell wall content produced. Generally, there will be present in the reaction, from about 3.5 percent to about 21.0 percent polymethylene polyphenylisocyanate and from about 1.5 percent to about 9.0 percent amine, relative to the weight of the water-immiscible material. Preferably, there will be from about 5.6 to about 13.9 percent polymethylene polyphenylisocyanate and from about 2.4 to about 6.1 percent amine and more particularly, 7.0 percent polymethylene polyphenylisocyanate and 3.0 percent amine relative to the weight of the water-immiscible material, present in the reaction. Although a stoichiometric amount of polyfunctional amine relative to the amount of polymethylene polyphenylisocyanate has been used herein, it should be recognized that excess polyfunctional amine may be used without departing from the spirit or scope of the present invention.

The emulsifying agents, being generally referred to herein as emulsifiers, which are critical for use in the practice of the present invention are the salts of lignin sulfonate, e.g., the sodium, potassium, magnesium, calcium or ammonium salts. In the practice of the process of the present invention, the sodium salt of lignin sulfonate is the preferred emulsifier. Any commercially available emulsifier of the type previously described which does not contain added surfactant, may be conveniently employed and many are described in McCutcheon's Detergents and Emulsifier's, North American Edition 1978 (McCutcheon Div., MC Publishing Co., Glen Rock, N.J.). Commercially available emulsifiers which may be mentioned are: Treax ®, LTS, LTK and LTM, respectively, the potassium, magnesium and sodium salts of lignosulfonate (50% aqueous solutions), Scott Paper Co., Forest Chemical Products; Marasperse CR ® and Marasperse CBOS-3 ®, sodium lignosulfonate, American Can Co.; Polyfon O ®, Polyfon T ®, Reax 88B ®, Reax 85B ®, sodium salts of lignin sulfonate and Reax C-21 ®, calcium salt of lignin sulfonate, Westvaco Polychemicals.

The range of emulsifier concentration found most acceptable in the system will vary from about ½ percent to about 15 percent and preferably from about 2 percent to about 6 percent, based on the weight of the water-immiscible material. Sodium lignosulfonate emulsifier is preferentially employed at a concentration of 2 percent relative to the weight of the water-immiscible material. Higher concentrations of emulsifier may be used without increased ease of dispersability.

The microcapsules of the present invention require no additional treatment such as separation from the aqueous liquid, but may be directly utilized or combined with, e.g., liquid fertilizers, insecticides or the like to form aqueous solutions which may be conveniently applied in agricultural uses. Most often it is most convenient to bottle or can the aqueous suspension containing the encapsulated water-immiscible material, in which case, it may be desirable to add formulation ingredients to the finished aqueous solution of microcapsules. Formulation ingredients such as thickeners, biocides, surfactants, dispersants, salts, anti-freeze agents and the like can be added to improve stability and ease of application.

The process of the present invention is capable of satisfactory performance and production of encapsulated material without adjustment to a specific pH value. That is, no adjustment of the pH of the system need be made during the encapsulation process. If it is desired to adjust the pH of the finished microcapsule formulation, as, for example, when the aqueous solution of finished microcapsule is combined with other herbicides, pesticides, etc., conventional cooperating reagents or additions for adjustment of acidity or alkalinity, or like characteristics, may be used, e.g., such substances as hydrochloric acid, sodium hydroxide, sodium carbonate, sodium bicarbonate and the like.

In the practice of the process of the invention, the temperature should be maintained above the melting point of the water-immiscible material but below the temperature wherein the polymeric shell wall will begin to hydrolyze excessively. For example, where it is desired to encapsulate a liquid organic solvent the temperature of the process may be maintained at room temperature; where it is desired to encapsulate a solid herbicide, it will be necessary to heat the herbicide to its molten state. Alachlor herbicide, for example, melts at 39.5° C. to 41.5° C. and the temperature of the process should accordingly be maintained above about 41.5° C. In general, the temperature of the reaction should not exceed above about 80° C., since the polymeric isocyanate monomer will begin to rapidly hydrolyze above this temperature, with resulting loss of formation of shell wall material.

The agitation employed to establish the dispersion of water-immiscible phase droplets in the aqueous phase may be supplied by any means capable of providing suitably high shear, that is, any variable shear mixing apparatus (e.g., blender) can be usefully employed to provide the desired agitation.

The desired condensation reaction at the interface between the water-immiscible phase droplets and the aqueous phase occurs very rapidly and within minutes, the condensation reaction is complete. That is, the formation of the polyurea capsule wall has been completed, thereby encapsulating the water-immiscible material within a skin of polyurea and there exists a useable encapsulated product suspended in an aqueous liquid.

The particle size of the microcapsules will range from about 1 micron up to about 100 microns in diameter. In general, the smaller the particle size the better. From about 1 to about 10 microns is an optimum range. From about 5 to about 50 microns is satisfactory for formulating.

Particle size is controlled by the emulsifier used and the degree of agitation employed. One convenient manner of controlling the size of the microcapsules is by adjusting the speed of agitation employed, which is supplied to form the dispersion of the water-immiscible phase droplets in the aqueous phase. The greater the speed of agitation at this stage, the smaller the capsules being obtained. Control of capsule size by adjustment of the rate of agitation is well within the skill of the art.

The present invention will be further explained by reference to the following examples which are merely illustrative and not limiting in nature. Unless otherwise stated, no change in particle size of the finished microcapsules or herbicide crystal formation in the aqueous suspending medium was observed with passage of time.

EXAMPLE 1

| Ingredients | Percent | Grams |
| --- | --- | --- |
| Technical triallate (96%) | 30.5 | 200.0 |
| PAPI-135 ® | 2.7 | 13.9 |
| 40% HMDA | 3.0 | 15.1 |
| Reax 88 B ® | 0.8 | 4.0 |
| Ammonium Sulfate | 26.1 | 132.0 |
| Water | 27.9 | 141.3 |
| TOTAL | 100.0 | 506.3 |

200 g of technical triallate containing 13.9 g. of PAPI-135 ® was emulsified into 141.3 g of water containing 4.0 g. of Reax 88 B ® sodium lignosulfonate. Technical triallate and PAPI-135 ® were maintained at 50° C.; the aqueous solution containing the sodium lignosulfonate emulsifier was at 50° C. The emulsion was formed with a Waring blender operated at high shear. To the emulsion was added 15.1 g of 40% HMDA with concurrent reduction of shear. After 20 minutes, 132.0 g of ammonium sulfate was added and the formulation was bottled. The particle size of the resulting microcapsules ranged from 1 to 10 microns in diameter. The resulting formulation contains 500 grams of encapsulated technical triallate per liter of aqueous solution.

EXAMPLE 2

| Ingredients | Percent | Grams |
| --- | --- | --- |
| Technical alachlor (91%) | 49.2 | 200.0 |
| PAPI ® | 3.7 | 15.0 |
| 35% HMDA | 4.9 | 20.0 |
| Reax 88 B ® | 0.9 | 3.8 |
| Water | 41.3 | 168.0 |
| Total | 100.0 | 406.8 |

200 g of technical alachlor maintained at 50° C., containing 15.0 grams of PAPI ® was poured into 168.0 g of water containing 3.8 g of Reax 88 B ®, sodium lignosulfonate emulsifier. An emulsion was formed in a square beaker utilizing a Brinkman Polytron Homogenizer, at high shear (the temperature inside the beaker rose to 60° C. as a result of the shear rate). To the emulsion was added 20.0 g of 35% HMDA with simultaneous reduction of shear to a slow rate. The resulting formulation contained 527 grams of encapsulated technical alachlor per liter of aqueous solution. The resulting microcapsules were 1–10 microns in diameter, particle size. About 20% liquid layer occurred with time but was resuspended with gentle shaking.

EXAMPLE 3

| Ingredient | Percent | Grams |
| --- | --- | --- |
| Technical alachlor (91%) | 49.0 | 200.0 |
| PAPI ® | 3.7 | 15.0 |
| 40% HMDA | 4.0 | 16.5 |
| Reax 88 B ® | 0.9 | 3.8 |
| Water | 38.2 | 155.9 |
| Ethylene Glycol | 4.2 | 17.1 |
| Total | 100.0 | 408.3 |

200.0 g of technical alachlor containing 15.0 g of PAPI ® was emulsified into 155.9 g of water containing 3.8 g of Reax 88B ® sodium lignosulfonate. Technical alachlor and PAPI ® were maintained at 50° C.; the aqueous solution containing the sodium lignosulfonate emulsifier was at room temperature. The emulsion was formed with a Waring blender operated at high shear. To the emulsion was added 16.5 g of 40% HMDA with concurrent reduction of shear. After 20 minutes, 17.1 g of ethylene glycol was added and the formulation was bottled. Settling occurred with time but gentle agitation fully resuspended the settled layer. Only a trace of material greater than 45 microns was observed when the formulation was passed through a 325 mesh screen (45 micron opening).

The procedure of Example 3 was repeated using various lignin sulfonate emulsifiers in place of Reax 88B ® ; the lignin sulfonate emulsifiers were: Reax 85A ®, Reax C-21 ®, Marasperse CX ®, Polyfon H ®, Polyfon O ®, Polyfon T ®, Reax 84A and Marasperse CBOS-3 ®.

EXAMPLE 4

| Ingredients | | Percent | Grams |
|---|---|---|---|
| Technical propachlor (96.6%) | | 46.4 | 100.0 |
| PAPI ® | | 3.5 | 7.5 |
| 35.8% HMDA | | 4.3 | 9.3 |
| Reax 88 B ® | | 0.9 | 2.0 |
| Water | | 44.9 | 96.6 |
| | Total | 100.0 | 215.4 |

All starting materials and the Waring blender cups were maintained at 70° C. 100.0 g of technical propachlor (96.6%) containing 7.5 g of PAPI ® was emulsified into 96.6 g of water containing 2.0 g of Reax 88 B ®, sodium lignosulfonate using a Waring blender operating at high shear. To the emulsion was added 9.3 g of 35.8% HMDA with concurrent reduction of shear. Capsules ranging from 1 to 60 microns in diameter, with the majority being 1 to 20 microns, were produced.

EXAMPLE 5

| Ingredients | | Percent | Gram |
|---|---|---|---|
| Technical butachlor (90%) | | 50.8 | 100.0 |
| PAPI ® | | 3.8 | 7.5 |
| 35.8% HMDA | | 4.7 | 9.3 |
| Reax 88 B ® | | 1.0 | 2.0 |
| Water | | 39.7 | 77.9 |
| | Total | 100.0 | 196.7 |

100.0 g of technical butachlor (90%) containing 7.5 g of PAPI ® (both at room temperature) was emulsified into 152.4 g of H₂O containing 2.0 g of Reax 88 B ® sodium lignosulfonate emulsifier using high shear. To the emulsion was added 9.3 g of 35.8% HMDA with concurrent reduction of shear. Spherical and irregularly-shaped particles ranging in size of from 1 to 30 microns in diameter, with the majority being 1–20 microns, were observed.

EXAMPLE 6

| Ingredients | | Percent | Grams |
|---|---|---|---|
| Technical alachlor (90%) | | 49.4 | 200.0 |
| PAPI ® | | 3.7 | 15.0 |
| 40% HMDA | | 4.1 | 16.7 |
| Reax 88 B ® | | 0.9 | 3.8 |
| Water | | 37.7 | 152.4 |
| Ethylene glycol | | 4.2 | 17.1 |
| | Total | 100.0 | 405.0 |

This example was prepared as in Example 2 except that a Ross Model 100L Homogenizer was used and the beaker was placed in an ice bath so that the temperature did not rise above 50° C. High shear was continued throughout. Shear was continued for 20 minutes and thereafter 17.1 grams of ethylene glycol was added just prior to bottling. Approximately all particles produced were less than 45 microns in diameter; only a trace of material did not pass through a 325 mesh screen (45 micron maximum openings).

EXAMPLE 7

| Ingredients | | Percent | Grams |
|---|---|---|---|
| Technical alachlor (93%) | | 45.5 | 200 |
| PAPI-135 ® | | 3.2 | 13.9 |
| BHMTA (70%) | | 3.4 | 15.1 |
| Reax 88 B ® | | 0.9 | 4.0 |
| NaCl | | 9.3 | 41.0 |
| Water | | 37.7 | 166.1 |
| | Total | 100.0 | 440.1 |

200.0 g of technical alachlor containing 13.9 g of PAPI-135 ® was emulsified into 166.1 g of water containing 4.0 g of Reax 88 B ® sodium lignosulfonate. All ingredients were maintained at 50° C. The emulsion was formed with a Waring blender operated at high shear. To the emulsion was added 15.1 g of 70% BHMTA with concurrent reduction of shear. After 20 minutes, 41.0 g of sodium chloride was added and the formulation was bottled. The resulting microcapsules were primarily spherical, with some irregularly shaped particles, and ranged in size from 1 micron to 15 microns in diameter, with the majority of the particles being 1 to 10 microns in diameter.

EXAMPLE 8

| Ingredients | | Percent | Grams |
|---|---|---|---|
| Technical alachlor (90%) | | 47.8 | 200.0 |
| Mondur MR ® | | 3.6 | 15.0 |
| HMDA (40%) | | 4.0 | 16.7 |
| Reax 88 B ® | | 0.9 | 3.8 |
| Water | | 39.6 | 165.4 |
| Ethylene glycol | | 4.1 | 17.1 |
| | Total | 100.0 | 418.0 |

Into 165.4 grams of water containing 3.8 grams Reax 88 B ® (both at room temperature) was emulsified 200.0 grams of technical alachlor (90%) containing 15.0 grams of Mondur MR ® at 50° C. The emulsion was formed with a Waring blender operating at high shear. To the emulsion was added 16.7 grams of HMDA (40%) with concurrent reduction of shear to provide gentle stirring. After 20 minutes, ethylene glycol was added. Irregular-shaped particles were 1–20 microns in diameter, with the majority being 1–10 microns in diameter.

EXAMPLE 9

| Ingredients | | Percent | Pounds |
|---|---|---|---|
| Technical alachlor (90%) | | 49.4 | 100.0 |
| PAPI ® | | 3.7 | 7.5 |
| HMDA (40%) | | 4.4 | 9.0 |
| Reax 88 B ® | | 0.9 | 1.9 |
| Water | | 37.4 | 75.5 |
| Ethylene glycol | | 4.2 | 8.6 |
| | Total | 100.0 | 202.5 |

Into a 55 gallon drum was added 100 pounds of technical alachlor (90%) at 60° C. and into the alachlor was dissolved 7.5 pounds of PAPI ® utilizing a Ross Model Me-105 Homogenizer. 75.5 pounds of water containing 1.9 pounds of Reax 88 B ® was added to the drum without shear. Thereafter, an emulsion was formed using the Ross Homogenizer to provide shear. To the emulsion was added 9.0 pounds of 40% HMDA. After 20 minutes, 8.6 pounds of ethylene glycol was added and the formulation was packaged in gallon containers. Mostly spherical particles with some irregular shapes were formed which were 1–60 microns in diameter with the majority being 1–20 microns in diameter.

EXAMPLE 10

| Ingredients | Percent | Grams |
|---|---|---|
| Technical alachlor (90%) | 46.8 | 200.0 |
| PAPI-135 ® | 1.6 | 7.0 |
| HMDA (40%) | 1.8 | 7.6 |
| Reax 88 B ® | 0.9 | 3.8 |
| Water | 39.6 | 169.0 |
| Sodium chloride | 9.3 | 39.7 |
| Total | 100.0 | 427.1 |

In this example all materials except the sodium chloride and 40% HMDA were at 50° C. Into 169.0 grams of water containing 3.8 grams of Reax 88 B ® was emulsified 200 grams of technical alachlor (90%) containing 7.0 grams of PAPI-135 ® with a Waring blender operating at high shear. To the emulsion was added 7.6 grams of HMDA (40%) with concurrent reduction of shear sufficient to provide gentle stirring. After 20 minutes, 39.7 grams of sodium chloride was added to balance the density of the aqueous phase with that of the suspended microcapsules. Both spherical and irregular-shaped microcapsules were produced ranging in size from 1 to 20 microns in diameter with some particles being up to 80 microns in diameter.

Example 10 was repeated using diethylenetriamine, triethylenetetraamine, tetraethylenepentamine and pentamethylenehexamine singly and in combination with 1,6-hexamethylenediamine. The amine combinations and concentration of each are described in Table I along with the additional water required, if any.

TABLE I

| 40% 1,6-Hexamethylenediamine (grams) | Diethylenetriamine (grams) | Water (grams) |
|---|---|---|
| 16.4 | 0.1 | 0 |
| 15.8 | 0.22 | 0.7 |
| 15.0 | 0.43 | 1.3 |
| 12.5 | 1.1 | 3.1 |
| 8.4 | 2.2 | 6.1 |
| 0 | 4.3 | 13.4 |
| Triethylaminetetramine | | |
| 16.4 | 0.1 | 0 |
| 15.8 | 0.24 | .7 |
| 15.0 | 0.48 | 1.2 |
| 12.5 | 1.2 | 3 |
| 8.4 | 2.4 | 5.9 |
| 0 | 4.8 | 13.9 |
| Tetraethylenepentamine | | |
| 16.4 | 0.1 | 0 |
| 15.8 | 0.26 | 0.6 |
| 15.0 | 0.52 | 1.2 |
| 12.5 | 1.3 | 2.9 |
| 8.4 | 2.6 | 5.7 |
| 0 | 5.2 | 11.5 |
| Pentamethylenehexamine | | |

TABLE I-continued

| 40% 1,6-Hexamethylenediamine (grams) | Diethylenetriamine (grams) | Water (grams) |
|---|---|---|
| 16.4 | 0.1 | 0 |
| 15.8 | 0.28 | .7 |
| 15.0 | 0.55 | 1.2 |
| 12.5 | 1.4 | 2.8 |
| 8.4 | 2.8 | 5.5 |
| 0 | 5.5 | 11.2 |

EXAMPLE 11

The microcapsules of this example were prepared according to the procedure of Example 10, except that the amount of PAPI ® and 40% HMDA was varied to produce from 6% to 30% shell wall content relative to the amount of herbicide encapsulated.

| | | | | % Shell Wall Content | | | | | |
|---|---|---|---|---|---|---|---|---|---|
| Grams | 7 | 8 | 9 | 10 | 11 | 12 | 15 | 20 | 30 |
| PAPI ® | 8.3 | 9.8 | 11.2 | 12.5 | 13.9 | 15.3 | 16.7 | 20.9 | 27.8 | 41.7 |
| HMDA (40%) | 9.1 | 10.6 | 12.1 | 13.6 | 15.0 | 16.6 | 18.2 | 22.8 | 30.0 | 45.3 |
| H₂O | 166.6 | 164.0 | 161.5 | 159.0 | 156.7 | 154.2 | 151.4 | 142.8 | 132.1 | 125.4 |

EXAMPLE 12

| Ingredients | Percent | Grams |
|---|---|---|
| Monochlorobenzene | 52.2 | 200.0 |
| PAPI ® | 3.6 | 13.9 |
| HMDA (40%) | 3.9 | 15.1 |
| Reax 88 B ® | 1.0 | 4.0 |
| Water | 39.3 | 150.0 |
| Total | 100.0 | 383.0 |

This example illustrates the encapsulation of an organic solvent. The order of addition of ingredients was the same as that described in Example 1. All steps of this example were carried out at room temperature. A Waring blender was used to provide medium shear which was reduced to gentle agitation after diamine was added. The particle size of the microcapsules produced, ranged from 1–15 microns in diameter.

EXAMPLE 13

| Ingredients | Percent | Grams |
|---|---|---|
| Alachlor (93%) | 33.8 | 1351.4 |
| Metribuzin (95%) | 11.0 | 440.6 |
| PAPI-135 ® | 3.1 | 124.6 |
| HMDA 40% | 3.4 | 135.3 |
| Reax 88 B ® | 0.9 | 35.8 |
| NaCl | 11.3 | 452.7 |
| Water | 36.5 | 1459.6 |
| Total | 100.0 | 3975.0 |

Into 1459.6 g water containing 35.8 g of Reax 88B ® sodium lignosulfonate emulsifier, was emulsified a solution of 1351.4 g of alachlor, 440.6 g of metribuzin and 124.6 g of PAPI-135 ®, all at 50° C. An emulsion was formed with a Polytron PT 1020 and Premier dispersator in a square vessel. To the emulsion was added 135.3 g of 40% HMDA and immediately thereafter Polytron shear was stopped. After 10 minutes, 452.7 g of NaCl was dissolved into the suspension which was then bottled. The particle size of the resulting spherical microcapsules ranged from 1-10 microns in diameter.

EXAMPLE 14

| Ingredients | Percent | Grams |
|---|---|---|
| Alachlor (93%) | 32.0 | 1254.4 |
| Linuron (92%) | 12.0 | 469.2 |
| PAPI-135 ® | 3.1 | 119.8 |
| HMDA 40% | 3.3 | 130.1 |
| Reax 88 B ® | 0.9 | 34.5 |
| NaCl | 11.8 | 460.0 |
| Water | 36.9 | 1446.4 |
| Total | 100.0 | 3914.4 |

Preparation conditions were identical to Example 12. The resulting microcapsules were spherical and ranged from 1-10 microns in diameter.

EXAMPLE 15

| Ingredients | Percent | Grams |
|---|---|---|
| Parathion (98.5%) | 38.8 | 200.0 |
| PAPI-135 ® | 2.7 | 13.9 |
| HMDA 40% | 2.9 | 15.1 |
| Reax 88B ® | 1.7 | 8.6 |
| NaNO₃ | 17.7 | 91.1 |
| Water | 36.2 | 187.0 |
| Total | 100.0 | 515.7 |

Into 187.0 g of water containing 8.6 g of Reax 88 B ® sodium lignosulfonate was emulsified 200.0 g of parathion containing 13.9 g of PAPI-135 ® dissolved therein; all ingredients were at 50° C. An emulsion was formed in a Waring blender using a Polytron PT 1020 to provide shear. To the emulsion was added 15.1 g of 40% HMDA and Polytron shear was stopped. After 5 minutes 91.1 g of NaNO₃ was dissolved into the suspension using the blender to provide gentle shear. The resulting microcapsules were spherical and ranged from 1-10 microns in diameter.

EXAMPLE 16

Comparisons of the herbicidal activity of alachlor encapsulated according to the process of this invention versus non-encapsulated alachlor indicate that in general, encapsulated alachlor exhibits comparable herbicidal activity against grass and broadleaf weeds. The crop safety of encapsulated alachlor was similar to that of non-encapsulated alachlor with microencapsulated alachlor exhibiting a greater degree of safety on cotton than the non-encapsulated alachlor. Table II summarizes the results observed at 6 weeks after application of encapsulated and non-encapsulated alachlor, at three rates of application, in tests done in Brazil according to standard agricultural procedures.

TABLE II

| | | % Control (Injury) | | | | | | | |
|---|---|---|---|---|---|---|---|---|---|
| Herbicide | (Kg Act. Ingr./Ha) | Soybeans | Cotton | Peanuts | Corn | Acanthospermum hispidum[1] | Conchrus[2] echinatus | Bidens[3] pilosa | Digitaria[4] sanguinalis | Brachiaria[5] plantaginae |
| Alachlor | 3.36 | 0 | 53 | 0 | 0 | 97 | 75 | 100 | 100 | 0 |
| Alachlor | 5.04 | 0 | 93 | 2 | 0 | 99 | 95 | 50 | 98 | 43 |
| Alachlor | 6.72 | 0 | 92 | 3 | 0 | 93 | 97 | 100 | 99 | 75 |
| Alachlor - Encapsulated | 3.36 | 0 | 5 | 3 | 0 | 58 | 83 | 100 | 98 | 68 |
| Alachlor - Encapsulated | 5.04 | 0 | 50 | 0 | 2 | 85 | 92 | 100 | 98 | 94 |
| Alachlor - Encapsulated | 6.72 | 0 | 7 | 0 | 0 | 99 | 99 | 100 | 100 | 99 |

[1]*Acanthospermum hispidum*: Average infestation 12 plants/m²
[2]*Conchrus echinatus*: Average infestation 7 plants/m², missing in some plots
[3]*Bidens pilosa*: Average infestation 6 plants/m², missing in some plots
[4]*Digitaria sanguinalis*: Average infestation 11 plants/m², missing in some plots
[5]*Brachiaria plantaginae*: Average infestation <10 plants/m², missing in some plots

EXAMPLE 17

Barnyardgrass, rough pigweed, yellow nutsedge, large crabgrass and green foxtail were planted in 9½"×5¼" aluminum pans. Alachlor* and microencapsulated technical grade alachlor were applied to duplicate pans at various rates. Both encapsulated and unencapsulated alachlor were applied to the pans using a belt sprayer utilizing water as a carrier. Two weeks after treatment (WAT) visual estimates of percent inhibition were made and recorded. The pans were allowed to dry out and the surface vegetation was removed. After removing the top ¼ inch of soil from each pan, the pans were replanted and covered with their original top ¼ inch of soil. No additional herbicide was applied. Two weeks after this second planting a second reading was taken. The replanting procedure was followed for an additional cycle for rates of 1, ½ and ¼ lb/acre. To improve fertility for the third cycle, 10 ml of standard nutrient solution was added to each pan. Final observations were made 48 days after initial treatment, i.e., approximately 7 weeks after treatment. The results are summarized in Table III and indicate that microencapsulated alachlor exhibits longer soil longevity than does unencapsulated alachlor, where applied at the same rates.

*The alachlor used in this example was a commercially-available emulsifiable concentrate sold by Monsanto Company under the trade name Lasso ®.

TABLE III

| | | % Inhibition (WAT)* | | | | | | | | | | | | | |
|---|---|---|---|---|---|---|---|---|---|---|---|---|---|---|---|
| | | Barn. Grass | | | R. Pig Weed | | | Y. Nut Sedge | | | L. Crab Grass | | | Gr. Fox Tail | | |
| Herbicide | Lb/A | 2 | 4 | 7 | 2 | 4 | 7 | 2 | 4 | 7 | 2 | 4 | 7 | 2 | 4 | 7 |
| Alachlor | 1.0 | 100 | 70 | 0 | 98 | 20 | 0 | 50 | 0 | 0 | 100 | 60 | 0 | 99 | 85 | 0 |

TABLE III-continued

| | | % Inhibition (WAT)* | | | | | | | | | | | | | |
|---|---|---|---|---|---|---|---|---|---|---|---|---|---|---|---|
| | | Barn. Grass | | | R. Pig Weed | | | Y. Nut Sedge | | | L. Crab Grass | | | Gr. Fox Tail | | |
| Herbicide | Lb/A | 2 | 4 | 7 | 2 | 4 | 7 | 2 | 4 | 7 | 2 | 4 | 7 | 2 | 4 | 7 |
| Alachlor | 0.5 | 100 | 35 | 0 | 95 | 0 | 0 | 50 | 0 | 0 | 100 | 35 | 0 | 90 | 50 | 0 |
| Alachlor | 0.25 | 100 | 0 | 0 | 90 | 0 | 0 | 0 | 0 | 0 | 99 | 0 | 0 | 80 | 20 | 0 |
| Alachlor | 0.125 | 100 | 0 | | 80 | 0 | | 0 | 0 | | 95 | 0 | | 75 | 0 | |
| Alachlor | 0.0625 | 100 | 0 | | 60 | 0 | | 0 | 0 | | 90 | 0 | | 70 | 0 | |
| Alachlor | 0.0312 | 95 | 0 | | 60 | 0 | | 0 | 0 | | 85 | 0 | | 70 | 0 | |
| Alachlor | 0.0156 | 80 | 0 | | 30 | 0 | | 0 | 0 | | 60 | 0 | | 40 | 0 | |
| Alachlor | 0.0078 | 50 | 0 | | 10 | 0 | | 0 | 0 | | 60 | 0 | | 30 | 0 | |
| Encapsulated Alachlor | 1.0 | 100 | 85 | 40 | 98 | 50 | 0 | 20 | 40 | 80 | 100 | 85 | 30 | 95 | 95 | 70 |
| Encapsulated Alachlor | 0.5 | 98 | 70 | 0 | 85 | 40 | 0 | 20 | 10 | 20 | 99 | 85 | 0 | 95 | 98 | 25 |
| Encapsulated Alachlor | 0.25 | 85 | 65 | 0 | 85 | 15 | 0 | 30 | 5 | 0 | 85 | 75 | 0 | 80 | 95 | 0 |
| Encapsulated Alachlor | 0.125 | 30 | 35 | | 90 | 0 | | 0 | 0 | | 60 | 40 | | 40 | 10 | |
| Encapsulated Alachlor | 0.0625 | 0 | 30 | | 85 | 0 | | 0 | 0 | | 30 | 30 | | 0 | 10 | |
| Encapsulated Alachlor | 0.0312 | 0 | 5 | | 70 | 0 | | 0 | 0 | | 25 | 0 | | 0 | 10 | |
| Encapsulated Alachlor | 0.0156 | 0 | 0 | | 65 | 0 | | 0 | 0 | | 50 | 0 | | 0 | 0 | |
| Encapsulated Alachlor | 0.0078 | 0 | 0 | | 40 | 0 | | 0 | 0 | | 30 | 0 | | 0 | 0 | |

*Weeks After Treatment

EXAMPLE 18

The herbicidal activity of microencapsulated and non-encapsulated triallate was compared on wild oats and blackgrass weeds in wheat stands at three European locations. The results summarized in Table IV indicate that encapsulated triallate exhibits comparable herbicidal activity as non-encapsulated triallate on wild oats and blackgrass. Encapsulated triallate exhibits as good or better crop safety on wheat as does non-encapsulated triallate. In the results summarized in Table IV the aqueous suspension of microencapsulated triallate and the nonencapsulated triallate were applied by spraying according to standard agricultural procedures.

TABLE IV

| | | % Inhibition (Injury) | |
|---|---|---|---|
| Herbicide | Rate (Kg/ha) | Wild Oats | Blackgrass |
| Triallate Sprayed | 1.5 | 57 | — |
| Triallate Sprayed | 1.5 | 17 | 26 |
| Triallate Sprayed | 1.5 | 23 | 0 |
| Triallate Sprayed | 2.25 | 70 | — |
| Triallate Sprayed | 2.25 | 37 | 40 |
| Triallate Sprayed | 2.25 | 24 | 34 |
| Encapsulated Triallate-Sprayed | 1.5 | 77 | — |
| Encapsulated Triallate-Sprayed | 1.5 | 77 | 26 |
| Encapsulated Triallate-Sprayed | 1.5 | 24 | 22 |
| Encapsulated Triallate-Sprayed | 2.5 | 85 | — |
| Encapsulated Triallate-Sprayed | 2.5 | 85 | 39 |
| Triallate-Sprayed | 2.5 | 62 | 40 |

In addition to the previously described advantages of the present invention, microencapsulation of herbicides or pesticides may, in general, offer several advantages over conventional herbicide or pesticide formulations. Thus, for example, microencapsulated herbicide formulations may reduce mammalian toxicity and extend the activity of the herbicide. Where volatility of the herbicide is a problem, microencapsulation can reduce evaporative losses and thus prevent reduction in herbicide activity associated with such losses. Microencapsulated herbicide formulations may, in some cases, be less phytotoxic to certain crop plants, thereby enhancing the crop safety of the herbicide. Microencapsulation of herbicides may also protect the herbicides from environmental degradation, reduce leaching of the herbicide into the soil and prolong or increase the soil life of the herbicide. It can be appreciated that microencapsulated herbicide formulations have several advantages which make such microencapsulated herbicide formulations a desirable and beneficial alternative to conventional herbicide formulations.

Accordingly, one object of the present invention is to provide a herbicidal composition consisting essentially of a suspension in water of microcapsules comprised of a herbicide contained within an encapsulating wall of polyurea. Herbicides of the type previously described are expressly contemplated for use in such compositions, preferably the acetanilide and thiolcarbamate type herbicides and particularly alachlor, butachlor, propachlor and triallate. The concentration of herbicide present in such compositions will be about 480 grams per liter of aqueous solution or greater, preferably from about 480 grams to about 700 grams per liter of aqueous solution and more preferably, from about 480 grams to about 600 grams per liter of aqueous solution.

The encapsulating wall of polyurea is the reaction product of polymethylene polyphenylisocyanate and a polyfunctional amine of the type previously described. The concentration of polymethylene polyphenylisocyanate will range from about 3.5 percent to about 21.0 percent relative to the weight of herbicide present in the composition and the concentration of polyfunctional amine will range from about 1.5 percent to about 9.0 percent relative to the weight of herbicide present in the composition.

Present in the water, in addition to the microcapsules, is a lignin sulfonate emulsifier of the type previously described and optionally, formulation ingredients such as anti-freeze agents, dispersing agents, salts, biocides and the like. The concentration of lignin sulfonate emulsifier may range from about ½ percent to about 15.0 percent relative to the weight of herbicide present in the composition.

It is to be understood that the present invention is not limited to the specific embodiments shown and described herein, but may be carried out in other ways without departure from its spirit or scope.

We claim:

1. A process for producing a composition consisting essentially of a mixture of water and microcapsules containing a water-immiscible material within a shell wall of polyurea, which process comprises:
   (a) providing an aqueous phase containing an emulsifier selected from the group consisting of the sodium, potassium, magnesium, calcium and ammonium salts of lignin sulfonate;
   (b) dispersing in said aqueous phase, a water-OOCH immiscible phase consisting essentially of polymethylene polyphenylisocyanate dissolved in said water-immiscible material, to form a dispersion of water-immiscible phase droplets throughout the aqueous phase;
   (c) adding, with agitation, to said dispersion a polyfunctional amine whereby said amine reacts with polymethylene polyphenylisocyanate to form a polyurea shell wall about said water-immiscible material.

2. A process as described in claim 1 wherein said emulsifier is the sodium salt of lignin sulfonate.

3. A process as described in claim 1 wherein said amine is 1,6-hexamethylene diamine.

4. A process as described in claim 3 wherein said emulsifier is the sodium salt of lignin sulfonate.

5. A process as described in claim 1 wherein said water-immiscible material is a herbicide.

6. A process as described in claim 1 wherein the temperature of the reaction is maintained above the melting-point of said water-immiscible material but below about 80° C.

7. A process as described in claim 1 wherein the average particle size of the microcapsules is in the range of from about 1 micron to about 50 microns in diameter.

8. A process as described in claim 1 wherein the concentration of said water-immiscible material is from about 480 grams to about 700 grams per liter of composition.

9. A process as described in claim 8 wherein the concentration of polymethylene polyphenylisocyanate is from about 3.5% to about 21.0% by weight of said water-immiscible material, wherein the concentration of said polyfunctional amine is from about 1.5% to about 9% by weight of said water-immiscible material and wherein the concentration of said emulsifier is from about ½% to about 15% by weight of said water immiscible material.

10. A process as described in claim 9 wherein said polyfunctional amine is 1,6-hexamethylene diamine and wherein said emulsifier is the sodium salt of lignin sulfonate.

11. A process as described in claim 9 wherein said water-immiscible material is a herbicide.

12. A process as described in claim 10 wherein said herbicide is an acetanilide or thiocarbamate herbicide.

13. A process as described in claim 12 wherein said herbicides are alachlor, butachlor, propachlor, triallate or diallate.

14. A process as described in claim 13 wherein said herbicide is alachlor, butachlor or triallate.

15. A process as described in claim 14 wherein said herbicide is alachlor.

16. A process as described in claim 14 wherein said herbicide is butachlor.

17. A process as described in claim 14 wherein said herbicide is triallate.

18. A process for producing a composition consisting essentially of a mixture of water and microcapsules containing a water-immiscible herbicide within a shell wall of polyurea, which process comprises:
   (a) providing an aqueous phase containing an emulsifier selected from the group consisting of the sodium, potassium, magnesium, calcium and ammonium salts of lignin sulfonate;
   (b) dispersing in said aqueous phase, a water-immiscible phase consisting essentially of polymethylene polyphenylisocyanate dissolved in said water-immiscible herbicide, to form a dispersion of water-immiscible phase droplets throughout the aqueous phase;
   (c) adding, with agitation, to said dispersion a polyfunctional amine whereby said amine reacts with polymethylene polyphenylisocyanate to form a polyurea shell wall about said water-immiscible herbicide;

wherein the concentration of water-immiscible herbicide is from about 480 grams to about 600 grams per liter of composition, wherein the concentration of polymethylene polyphenylisocyanate is from about 3.5% to about 21.0% by weight of said water-immiscible material, wherein the concentration of said polyfunctional amine is from about 1.5% to about 9.0% by weight of said water-immiscible material, and wherein the concentration of said emulsifier is from about ½% to about 15% by weight of said water-immiscible material.

19. A herbicidal composition consisting essentially of a mixture of water and microcapsules containing a water-immiscible herbicide, said mixture being produced by a process which comprises the steps of:
   (a) providing an aqueous phase containing an emulsifier selected from the group consisting of the sodium, potassium, magnesium, calcium and ammonium salts of lignin sulfonate;
   (b) dispersing in said aqueous phase, a water-immiscible phase consisting essentially of polymethylene polyphenylisocyanate dissolved in said water-immiscible herbicide, to form a dispersion of water-immiscible phase droplets throughout the aqueous phase;
   (c) adding, with agitation, to said dispersion a polyfunctional amine whereby said amine reacts with polymethylene polyphenylisocyanate to form a polyurea shell wall about said water-immiscible herbicide;

(d) wherein the concentration of said water-immiscible herbicide is from about 480 grams to about 700 grams per liter of said composition, wherein the concentration of polymethylene polyphenylisocyanate is from about 3.5% to about 21.0% by weight of said water-immiscible material, wherein the concentration of said polyfunctional amine is from about 1.5% to about 9.0% by weight of said water-immiscible herbicide, and wherein the concentration of said emulsifier is from about ½% to about 15% by weight of said water-immiscible herbicide.

20. A composition as described in claim 19 wherein said amine is 1,6-hexamethylene diamine.

21. A composition as described in claim 20 wherein said emulsifier is the sodium salt of lignin sulfonate.

22. A composition as described in claim 21 wherein said herbicide is selected from the group consisting of alachlor, butachlor, propachlor, triallate and diallate.

23. A composition as described in claim 22 wherein said herbicide is alachlor, butachlor or triallate.

24. A composition as described in claim 19 wherein the concentration of said herbicide is from about 480 grams to about 600 grams per liter of aqueous solution, wherein the concentration of polymethylene polyphenylisocyanate is from about 5.6% to about 13.9% relative to the weight of said herbicide, wherein the concentration of said polyfunctional amine is from about 2.4% to about 6.1% relative to the weight of said herbicide, and wherein the concentration of said emulsifier is from about 2.0% to about 6.0% relative to the weight of said herbicide.

25. A composition as described in claim 19 wherein the concentration of polymethylene polyphenylisocyanate is about 7.0% relative to the weight of said herbicide, wherein the concentration of said polyfunctional amine is about 3.0% relative to the weight of said herbicide and wherein the concentration of said emulsifier is about 2% relative to the weight of said herbicide.

26. A composition as described in claim 25 wherein said herbicide is alachlor.

27. A composition as described in claim 25 wherein said herbicide is triallate.

28. A composition as described in claim 25 wherein said herbicide is butachlor.

29. A composition as described in claim 19 wherein the average particle size of the microcapsules is in the range of from about 1 micron to about 50 microns in diameter.

* * * * *